United States Patent [19]
Glynn et al.

[11] 3,942,516
[45] Mar. 9, 1976

[54] BIOFEEDBACK TRAINING METHOD AND SYSTEM

[75] Inventors: Thomas W. Glynn, Beverly; J. Michael James, Cambridge, both of Mass.

[73] Assignee: Cyborg Corporation, Boston, Mass.

[22] Filed: Mar. 18, 1974

[21] Appl. No.: 452,215

[52] U.S. Cl. .......... 128/2.1 B; 35/22 R; 128/2.1 M; 128/2.05 R
[51] Int. Cl.² ...................... A61B 5/04; G09B 19/00
[58] Field of Search ... 35/22 R; 128/2.05 R, 2.06 R, 128/2.1 M, 2.1 B

[56] References Cited
UNITED STATES PATENTS

| | | | |
|---|---|---|---|
| 3,572,317 | 3/1971 | Wade | 128/DIG. 29 UX |
| 3,618,592 | 11/1971 | Stewart | 128/DIG. 29 UX |
| 3,774,593 | 11/1973 | Hakata et al. | 128/2.1 B |
| 3,814,082 | 6/1974 | Taylor | 128/2.06 R X |

OTHER PUBLICATIONS

"Biofeedback: Turning on the Power of Your Mind;" *Cosmopolitan Magazine*, Sept. 1972, p. 78.

*Primary Examiner*—Wm. H. Grieb
*Attorney, Agent, or Firm*—Morse, Altman, Oates & Bello

[57] ABSTRACT

A system and method are provided for use in training individuals in biofeedback techniques. A variety of physiological functions are monitored on separate channels and associated circuitry generates feedback signals for each function. The feedback signals from the various physiological functions preferably are combined in a matrix from which an output is generated only under predetermined conditions as when two or more of the monitored functions are within the parameters set for each separate function.

1 Claim, 9 Drawing Figures

BIOFEEDBACK TRAINING METHOD AND SYSTEM

BACKGROUND OF THE INVENTION

1. Field of the Invention

This invention relates generally to biofeedback techniques and equipment and more particularly is directed towards a new and improved biofeedback training method and associated system.

2. Description of the Prior Art

Biofeedback generally refers to an area of psychophysiological research and applications by which a subject is able to exert conscious control over certain autonomic systems. In general, the bioelectric signal generated by specific physiological change is amplified and the information concerning the change is fed back to the subject in a form by which the subject is able to monitor the change and in this fashion learn to control the function.

Heretofore, instruments employed for this purpose have been capable of monitoring single body functions such as brain wave activity, skin temperature, muscular activity and the like. The subject thus is provided with biofeedback data with respect to a single function only or a number of separate feedback signals. While instruments available heretofore for this purpose have provided the necessary feedback data, they have been lacking the ability to give one feedback signal which gives a profile of the complete physiological condition of the subject.

Accordingly, it is an object of the present invention to provide a new and improved method and associated system capable of monitoring a plurality of physiological functions and providing feedback data for each function in one mode, or, in another mode providing feedback data only when some or all of the individual functions are in pre-selected states.

SUMMARY OF THE INVENTION

This invention features a biofeedback training method comprising the steps of monitoring a plurality of different physiological functions to obtain feedback signals corresponding to the condition of each function and processing signals to generate feedback data only under certain predetermined conditions of at least two functions thereby allowing the subject to train in the simultaneous control over at least two biological functions.

This invention also features a biofeedback training system, comprising a plurality of separate input modules adapted to monitor a plurality of physiological functions that generate binary outputs therefrom, a matrix control unit is connected to each of said modules and is programmed to generate feedback signals to the subject only when the outputs of certain of said modules are in a predetermined state whereby the subject receives biofeedback signals useful in controlling simultaneously two or more biological functions. The system also includes new and improved modular biological sensors and associated circuitry.

DETAILED DESCRIPTION OF THE PREFERRED EMBODIMENT

Figure 1:
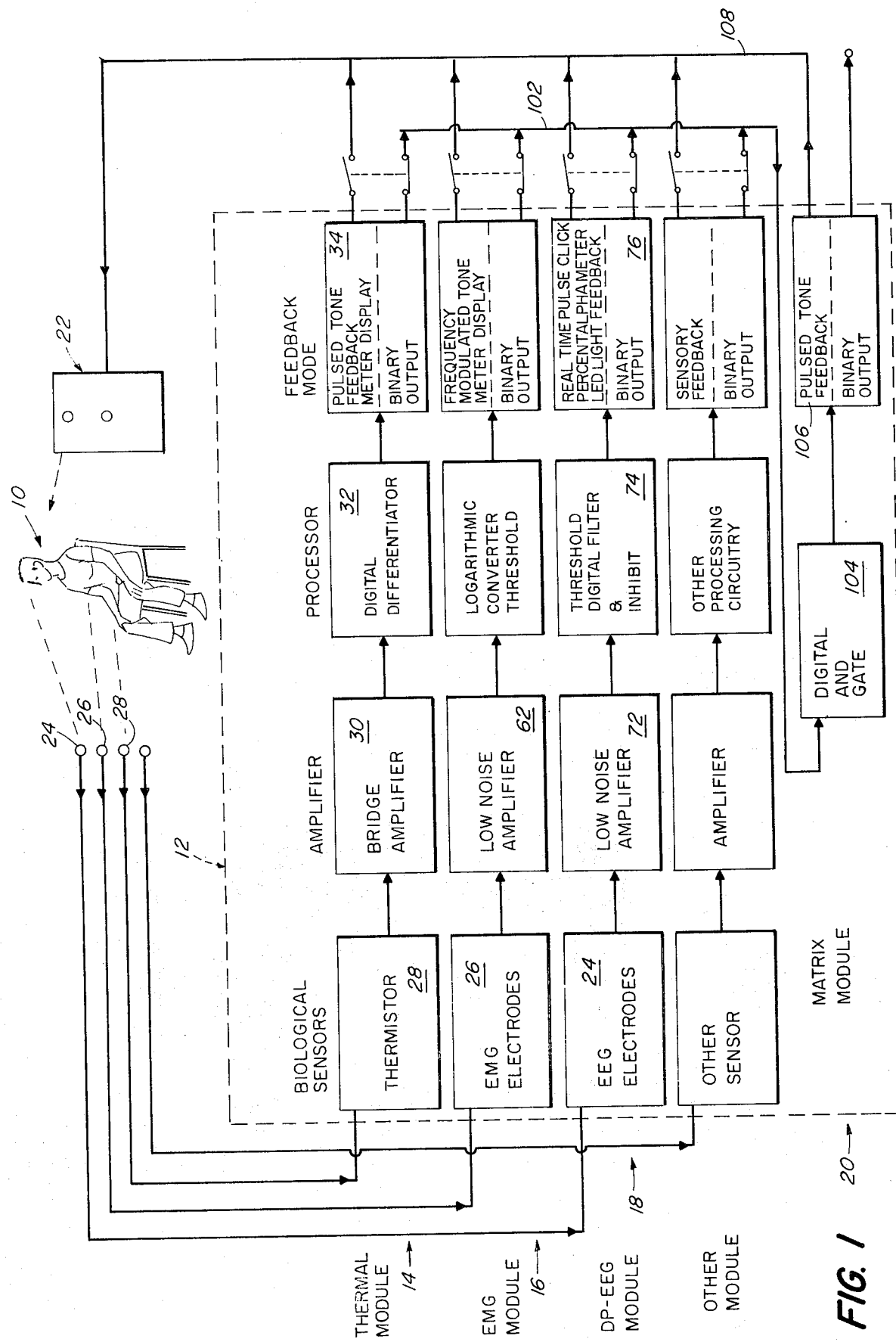
FIG. 1 is a somewhat schematic block diagram of a biofeedback system made according to the invention.

Current biofeedback training techniques have involved the monitoring of a single physiological function to obtain feedback data by which the subject is able to develop control, to a greater or lesser extent, over that function. In practice, the equipment employed to obtain the feedback data involves instrumentation adapted to monitor bioelectric signals from a specific physiological change, the signal being greatly amplified and processed for feeding back the information to the subject in visual or audible form. Biofeedback instruments currently available include thermal units adapted to provide feedback information with respect to the difference in skin temperature between two different locations on the body. With such instruments, the subject is able to gain some control over blood flow between the two locations. EMG units provide the feedback of myo-electric signals to give the subject information concerning muscular activity whose level is far below that of normal sensory awareness. EEG feedback units are employed to detect brain wave activity whereby the subject is able to train in altering his brain wave activity.

In all of the prior techniques the procedure has been to monitor but a single physiological function and hence biofeedback training has been limited to specific physiological functions. This practice is self-limiting insofar as it does not provide information for either the subject or an investigator as to when a particular combination of physiological changes is taking place. Also, the use of a single biofeedback unit does not provide a complete physiological profile of the subject or enable the subject to train in and develop control over a complex array of physiological variables simultaneously. Training with respect to a plurality of physiological variables can thus result in the elimination of system transferal which may occur in certain instances.

In accordance with the present invention a plurality of physiological functions are monitored simultaneously and signals generated by the monitoring instruments are processed and combined in a matrix. The operator sets the criteria that must be met by each physiological function being monitored, and, in this fashion, the subject will obtain feedback only when the state of the functions meet all of the programmed criteria. The difficulty of each separate criteria is continuously variable to allow the subject's responses to be shaped to obtain the desired result. The matrix allows the subject to demonstrate simultaneous control over two or more biological functions. By way of example, the system can be programmed to provide feedback only when the subject's brain waves are of a certain frequency and amplitude, differential skin temperature is changing in the desired direction, and muscle tension in one or more muscle groups is below a programmed level. The matrix feedback is not merely the feedback of many separate signals rather it reduces the attention level required by the subject insofar as he receives only one feedback signal rather than a plurality of signals representative of different functions.

Referring now to the drawing and to FIG. 1 in particular, there is illustrated by diagram a system made according to the invention and involving a plurality of physiological sensors adapted to monitor a plurality of different physiological functions. The sensors and associated circuitry are arranged in separate channels according to the monitored function with all of the channels connected to a common matrix prior to being sent back to the subject. In the drawings, the subject is generally indicated by reference character 10 and the system, generally indicated by reference character 12, is comprised of two or more separate channels. In the illustrated embodiment the system includes a thermal module 14, an EMG module 16 and a DP-EEG module 18, defining separate channels. Other modules defining other separate channels may be added to the system. All of the modules are connected to a matrix module 20 by which the system may be operated in a matrix mode in which the outputs of each channel are passed through the matrix module which combines data from the several channels and provides an output when the outputs of selected channels are in a predetermined state. The several channels may be operated separately, if desired, so that the subject may employ the system to monitor a single function only. The system output is to a sensory unit 22 which may include one or more sensory devices such as a sound emitter, a light emitter, a vibrator or the like, providing a feedback sensory input to the subject.

Each biofeedback module consists of a biological sensor such as an electrode 24, 26 and 28 connected directly to the subject 10. For the thermal module the sensor 28 may take the form of a thermistor while the EMG electrode 26 and the EEG electrode 24 are selected to sense and transmit muscular activity and brain wave activity, respectively. Each module also includes an amplifier by which the signals received by the biological sensors are greatly amplified and the outputs of the amplifiers are fed through processing circuitry and thence to a feedback section which provides the feedback signal in an appropriate mode.

The best form of feedback signal is considered to be one requiring the least mental processing on the part of the subject to determine whether or not training is taking place.

THERMAL MODULE

In the thermal module 14 this function is performed in a unique way. Basically, the thermal signal is a voltage that is proportional to the difference in temperature between two points on the subject 10. This signal is one that moves at an extremely slow rate and it is a particularly difficult matter to start the subject training in this area because of the slight variations generated when training is initiated. The thermal module 14 employs a sampling technique which avoids this difficulty. The thermal module samples the voltage and stores the value in a sample and hold circuit. As shown in the block diagram of FIG. 1, the biological sensor of thermal module is the thermistor 28, the output of which is greatly amplified by means of a bridge amplifier 30. The signal produced by the bridge amplifier is then fed into a digital differentiator 32. In the differentiator 32, the voltage is sampled and its value stored in a sample and hold circuit. This circuit is set to cycle periodically, typically 10 seconds, and then re-sample and hold a new voltage. The circuit then compares the two voltages and generates a pulsed tone feedback signal in a feedback unit 34. The circuit again cycles comparing the next two voltage samplings and generates a pulse tone feedback for the next 10 seconds, assuming the subject is training properly. The circuit constitutes a digital differentiator.

The technique is particularly useful in training insofar as the normal training method is to instruct the subject to imagine something such as holding his hand in cold water for a period of time.

Prior instruments for this purpose employ either meter feedback information which is not particularly effective because images are easier to hold with the eyes closed or use a frequency modulated tone feedback which does not indicate sharply small gradual changes. With the present system, however, not only are these drawbacks eliminated but, also, the mental processing required by the subject to determine his progress is reduced. The output of the module is also binary in nature which is useful in the matrix module 20.

Figure 4:
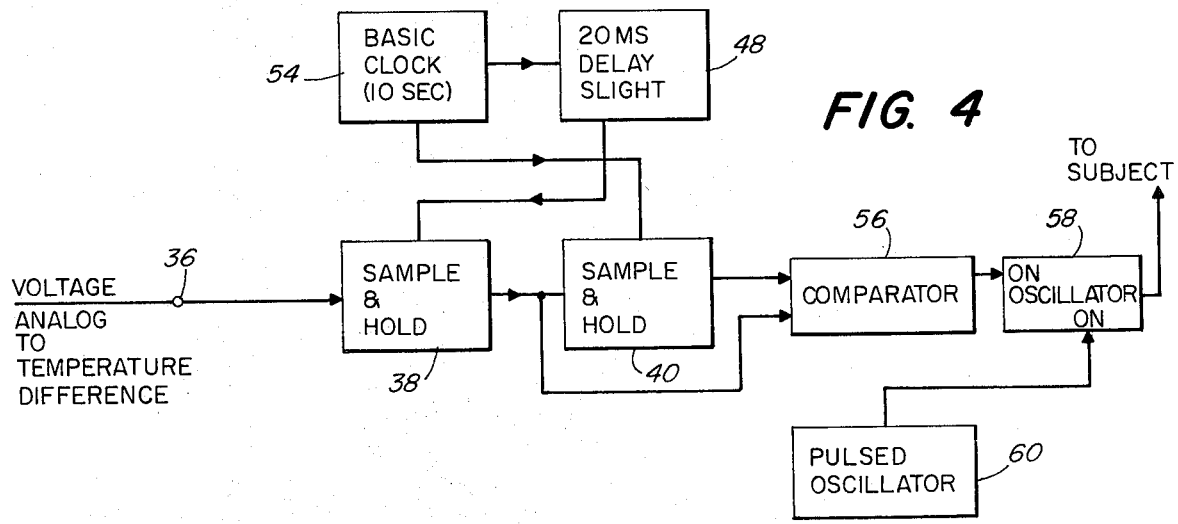
FIG. 4 is a block diagram of a thermal digital differentiator made according to the invention and employed in the thermal module of the system.
Figure 5:
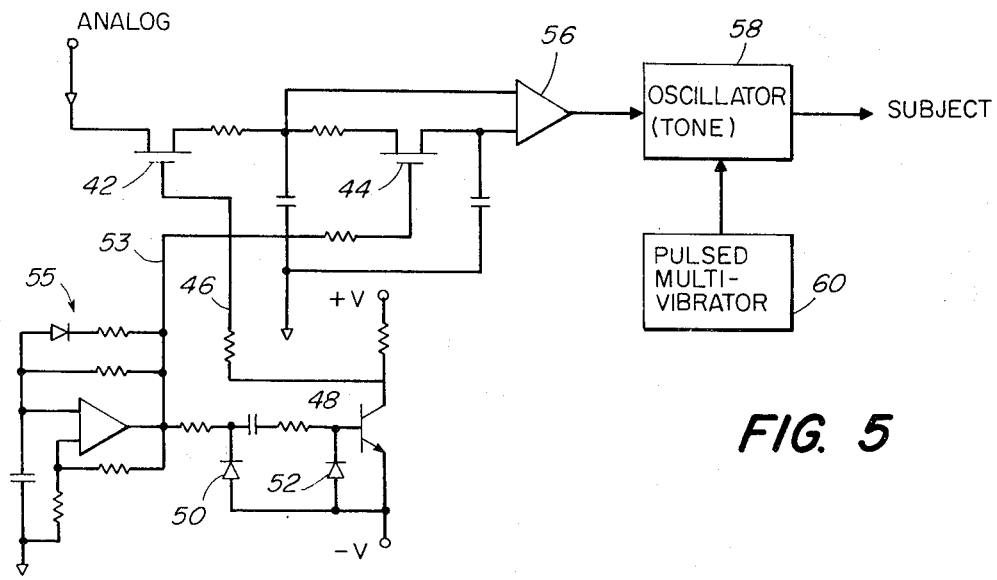
FIG. 5 is a circuit diagram corresponding to the block diagram of FIG. 4.

The thermal digital differentiator is illustrated in block form in FIG. 4 and in diagrammatic form in FIG. 5. In FIGS. 4 and 5, the input at a terminal 36 is a voltage from the bridge amplifier 30 and is analog to the temperature difference detected between two points on the subject 10. The analog voltage is fed into a first sample and hold circuit 38 having output to a second sample and hold circuit 40. Each sample and hold circuit includes a field effect transistor switch 42 and 44, respectively. The base of the field effect transistor switch 42 is connected by a lead 46 to a delay circuit of typically 20 ms, formed by means of a transistor 48 and a pair of diodes 50 and 52 that connects to the base junction. The base of the field effect transistor 44 is connected by a lead 53 to a basic clock circuit typically set for ten seconds indicated by reference character 55. The two sample and hold circuits 38 and 40 provide inputs to a comparator 56 the output of which is to a tone oscillator 58 also receiving inputs from a pulsed multi-vibrator 60. The output of the oscillator 58 is fed back to the subject directly or to the matrix 20, depending upon the particular mode of operation.

EMG MODULE

Figure 6:
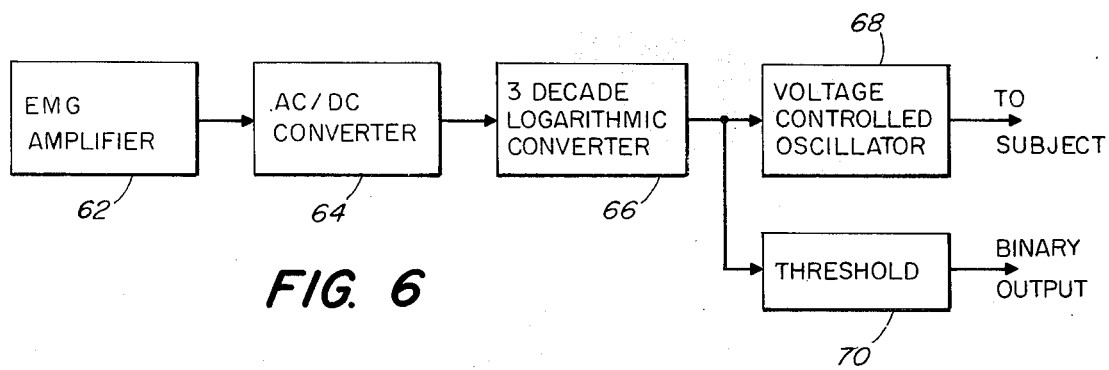
FIG. 6 is a block diagram of an EMG logarithmic converter employed in the EMG module of the system.

With respect to the EMG module a technique is employed which differs from that normally utilized in this field. Heretofore, the normal EMG biofeedback devices have integrated the EMG signals insofar as it is likely to be a more accurate measure of the total electrical activity in a muscle than is the amplitude of the waveform. It has been discovered that small electrical shocks applied to a muscle create tensions whose integrated EMG signal is proportional to the applied frequency of the shocks. The human body has been found to respond in a logarithmic fashion to sensing frequency-varying functions (i.e., musical octaves) so that the most likely useful feedback signal would be a signal that is proportional to the logarithm of the integrated EMG signal. The EMG module of the present system thus functions on that feedback basis. In the EMG module 16, as illustrated in FIGS. 1 and 6, the EMG electrodes 26, which are applied to the subject 10, provide a signal to a low noise amplifier 62. The EMG signal, which has been amplified, is detected and integrated through an AC to DC converter 64 and then shaped through a logarithmic amplifier 66, typically a three-decade logarithmic converter. The resulting signal provides separate inputs to a voltage controlled oscillator 68 and to a threshold circuit 70, the threshold circuit providing a binary output for the matrix while the oscillator 68 may be employed for direct feedback training to the subject. Conventional systems of this type use either a linear or diode shaped response while the present system employs a logarithmically shaped response.

EEG MODULE

Referring now to the EEG module 18, the EEG electrodes 24 connected to the subject provide input signals to a low noise amplifier 72 which, in turn, provides an amplified signal to a threshold digital filter and inhibit circuit 74. The output of this circuit is then fed to a feedback unit 76, which typically may include a real time pulse click percent alpha meter and/or a light emitting diode providing a light feedback for the subject 10. The unit 76 also includes a binary output for the matrix module 20.

The digital filter 74 (FIG. 7) allows a continuous tuning down to an extremely narrow band over the entire EEG range. The circuit is considerably simpler than conventional digital filters and, basically, the incoming signal from the amplifier 72 is passed through a threshold or zero crossing detector 78 provided with a potentiometer 80 for use in setting the threshold of the detector 78. The resulting pulse from the detector 78 is made uniform by passing it through a one-shot multivibrator 82. The result of the zero crossing pulse is used to turn on two re-triggable monostable multivibrators 84 and 86, each of which is provided with a potentiometer 88 and 90 for adjustment thereof. The multivibrator 84 is set at the pulse width of the high frequency end of the desired band while the multivibrator 86 is set at the pulse width of the low frequency end of the band. The output of the high vibrator 84 is inverted at 92 and summed in a Boolean sense with the output of the low multivibrator 86 and the zero crossing in an AND gate 94. The output of the AND gate used to perform this sum will be a pulse only when the input frequency to the AND gate 94 is between the low and high settings of the two multivibrators 84 and 86. If the frequency is too low, the low multivibrator will return to zero and cancel the output. The frequencies of the two multivibrators 84 and 86 are set by the calibrated potentiometers 88 and 90. The digital filter of the foregoing configuration is generally insensitive to noise, variations in supply voltage and is simple to operate.

Figure 7:
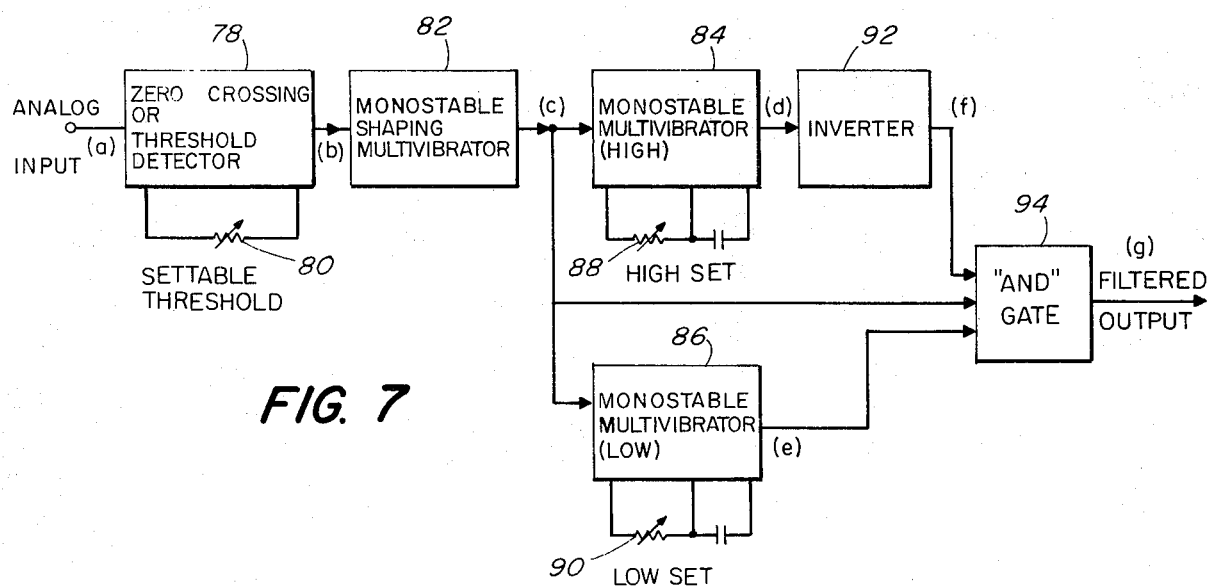
FIG. 7 is a block diagram of a digital filter employed in the EEG module of the system.
Figure 8:
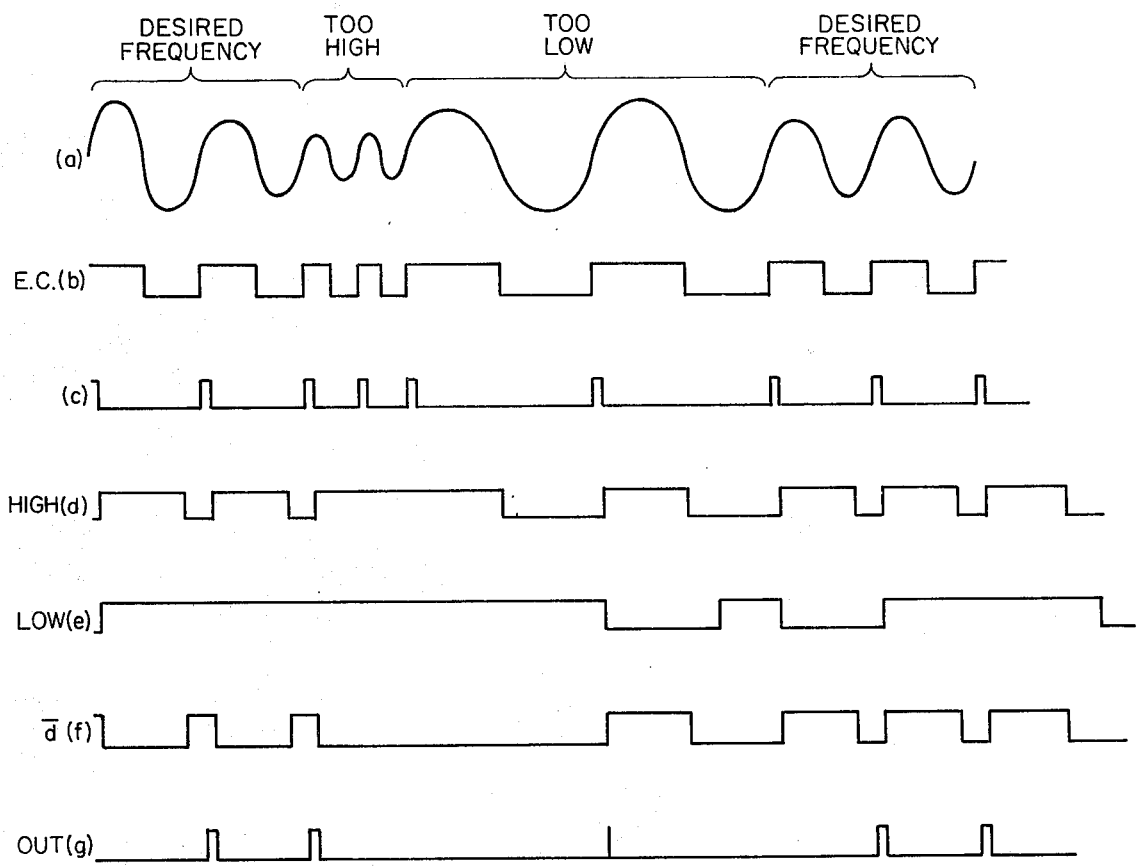
FIG. 8 is a wave formed diagram employed to illustrate the operation of the system, and, FIG. 9 is a logic diagram of inhibit circuitry employed in the invention.

In FIG. 8 the various alphabetically labeled waveforms correspond to the shape of the signals at similarly labeled points in the diagram of FIG. 7. In FIG. 8, it will be noted that output pulses (G) are present only when the frequency is in the desired range. This may be expressed by the equation $G = E + F$.

Two of the main difficulties encountered with biofeedback training based on brain wave activity relate to artifacts and pulse width training. The difficulties arising from artifacts is that, even with very tight band pass filters, there are numerable sources that can cause false feedback signals. Some of these are movement artifacts, electrode artifacts and the like. These artifacts interfere with successful training since they require that the subject learns to ignore them. This is a difficult task particularly while the subject is first starting in brain wave training and also introduces the possibility of biofeedback training based on an undesired function such as eye muscle tremor. With respect to pulse width training, the present techniques allow for amplitude training of the desired EEG waveform by way of thresholds or amplitude modulation and also frequency training through filters and percent of time training. No system, however, heretofore has been developed to do pulse width training. Under this technique the subject attempts to lengthen the actual bursts of desired signals. By using an inhibit circuitry in the EEG module 18 the subject is able to eliminate all artifacts and to train on pulse width.

Figure 9:
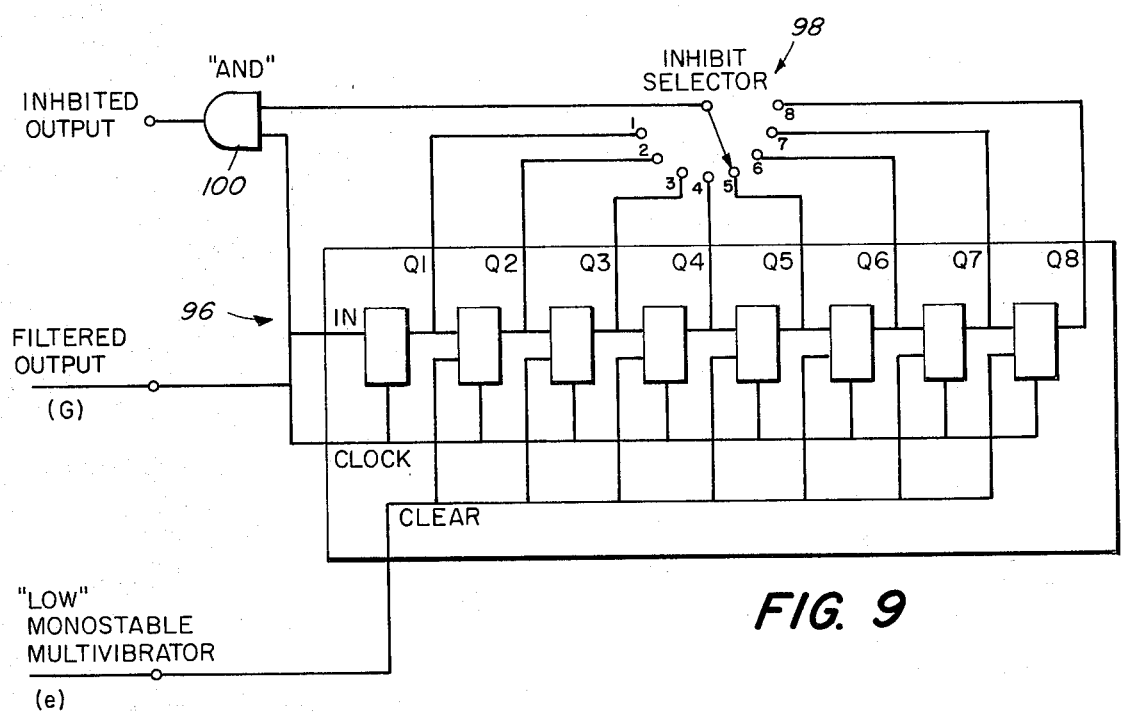

The inhibit circuitry shown in FIG. 9 receives input signals from the digital filter of FIG. 7. The output (G) of the digital filter serves as the input for an eight bit series in, parallel out shift register 96. The filtered signal (G) also serves as a clock pulse. The output (E) of the low monostable multivibrator 86 is used to clear the register 96 whenever it goes to an "O" state. The number of pulses inhibited is selected by a switch 98 which picks up positions Q1 through Q8 of the shift register output. This output is then ANDed by an AND gate 100 with the output of the digital filter. The output then will be the same pulse train that comes through the digital filter, but the leading pulses in the train will be inhibited up to the first eight depending upon the setting of the selector switch 98 which selects Q1 through Q8.

To use an artifict inhibitor the operator merely places the switch on one of the low numbers such as 2 or 3. It will normally be very unlikely that any artifacts will result and have a pulse train after filtering of more than two or three so that the inhibit selector can be set to eliminate all artifacts.

To use a pulse width trainer, the operator merely sets the selector on the highest number that gives no output. The training at this setting will provide feedback only when the operator lengthens the pulse that the subject is producing.

Other modules defining other biofeedback channels for different physiological functions may be added to the system.

MATRIX MODULE

All of the channels have outputs to the matrix module 20 through a lead 102. The matrix module 20 allows the researcher, clinician or individual to train on the basis of a complex array of physiological variables instead of a single physiological function. Most symptoms of psychosomatic disease have a number of physiological correlates. For example, a hypertense individual might have high blood pressure, a high level of muscle tension, a predominately Beta brain wave state and vasodilation of the head muscles. Instead of just EMG or Alpha training, the present system allows an individual to train all of the physiological variables at once. The system can be set to provide feedback only when the subject is relaxed muscularly below a certain level (EMG) and the vaso-dialation of the head is reducing (thermal) and he is in the Alpha state (EEG). This complex training is able to eliminate sympton transferal. The system thus is able to allow multiple parameter training either with multiple feedbacks or with one matrixed feedback.

Figure 2:
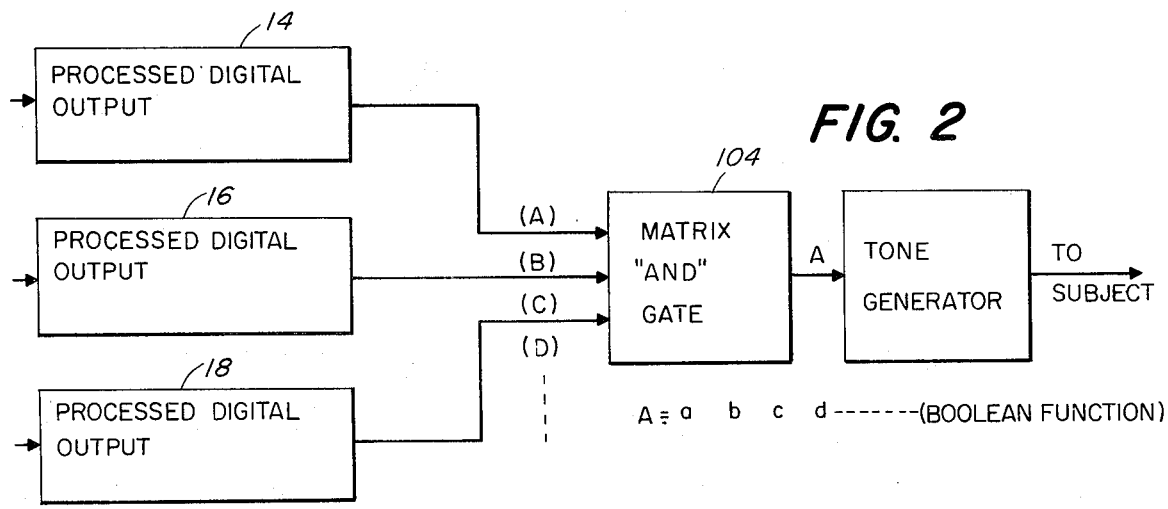
FIG. 2 is a block diagram of the matrix system employed in the FIG. 1 system.
Figure 3:
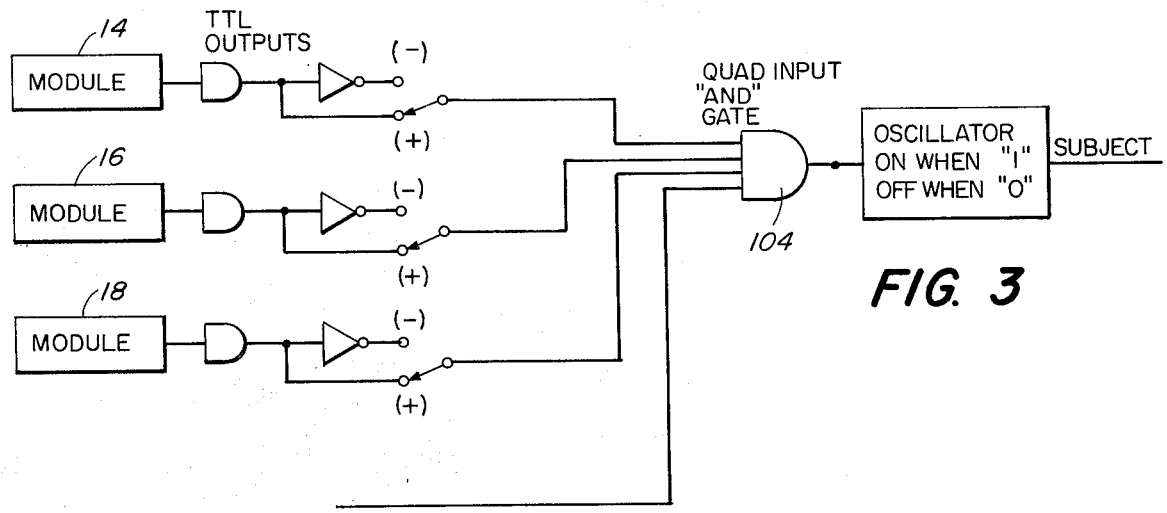
FIG. 3 is a circuit diagram corresponding to the block diagram of FIG. 2.

As best shown in FIGS. 2 and 3 the matrix module 20 is organized about a multiple input AND gate 104 receiving inputs from the various channels defined by modules 14, 16, 18, etc. The gate 104 will generate an output signal only when all of the selected channels deliver a pulse of the predetermined parameter and this output will be fed to a feedback device 106, typically in the form of an oscillator which is on when a 1 is present at its input and off when an 0 is present. This represents a pulsed tone feedback for the subject 10 and is fed through a lead 108 which is connected to the individual outputs of various channels and to the device 22. The unit 106 also is provided with a binary output.

Having thus described the invention what we claim and desire to obtain by Letters Patent of the United States is:

1. A closed loop system for use in the biofeedback training of a subject, comprising
    a. a plurality of discrete subsystems each adapted to monitor a different physiological function of said subject and generate status signals with respect thereto,
    b. a discrete biological sensor connected to each subsystem and adapted to be connected to said subject,
    c. matrix means connected to all of said subsystems for logically processing said status signals and generating a single feedback signal when at least two different selected status signals are at a predetermined value,
    d. sensory means for said subject connected to said matrix means and adapted to produce a sensory signal as a feedback sensory input to said subject upon generation of a feedback signal from said matrix means,
    e. each of said subsystems including amplifying means connected to each of said sensors for amplifying the output thereof, and analog to digital converting means connected to said amplifying means for converting analog signals from said amplifying means to digital signals for said matrix means,
    f. each of said subsystems including binary output means for said matrix means and said matrix means includes a logical AND gate connected to each of said subsystems and said sensory means and adapted to generate an output feedback signal only when predetermined status signals are at a predetermined value, and,
    g. switching means between each of said subsystems, said matrix means and said sensory means for selectively connecting any of said subsystems to either said matrix means or directly to said sensory means,
    h. said subsystems including a thermal module adapted to detect temperature differences between spaced points on said subject, an EMG module adapted to detect muscular activity of said subject and an EEG module adapted to detect brain wave activity of said subject,
    i. said thermal module including a digital differentiator for periodically sampling, storing and comparing status signals processed by said thermal module,
    j. said EMG module including a logarithmic converter adapted to provide a feedback signal logarithmically proportional to the status signals processed by said EMG module,
    k. said EEG module including a threshold digital filter providing a feedback signal only when the status signals processed by said EEG module are within a predetermined value.

* * * * *